(12) United States Patent
Shoji et al.

(10) Patent No.: US 7,342,994 B2
(45) Date of Patent: Mar. 11, 2008

(54) MAMMOGRAM RECORDING AND READ-OUT APPARATUS

(75) Inventors: Takashi Shoji, Kanagawa-ken (JP); Toshitaka Agano, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 109 days.

(21) Appl. No.: 11/128,172

(22) Filed: May 13, 2005

(65) Prior Publication Data

US 2005/0254620 A1    Nov. 17, 2005

(30) Foreign Application Priority Data

May 13, 2004    (JP)    ............... 2004-143580

(51) Int. Cl.
*A61B 6/04*    (2006.01)
(52) U.S. Cl. ............... 378/37; 128/915; 378/189
(58) Field of Classification Search ............... 378/37, 378/98.8, 114–116, 208; 128/845, 915; 250/580, 250/591
See application file for complete search history.

(56) References Cited

U.S. PATENT DOCUMENTS 4,233,516 A * 11/1980 Trepte ............... 378/181

| | | | |
|---|---|---|---|
| 6,339,636 B1 * | 1/2002 | Ogawa | 378/146 |
| 6,741,673 B2 * | 5/2004 | Kamenetsky et al. | 378/37 |
| 2004/0131145 A1 * | 7/2004 | Ohara | 378/37 |
| 2004/0170254 A1 * | 9/2004 | Gregerson et al. | 378/197 |
| 2005/0117709 A1 * | 6/2005 | Dippl et al. | 378/189 |
| 2006/0098777 A1 * | 5/2006 | Hoheisel | 378/98.8 |

FOREIGN PATENT DOCUMENTS

JP    5-173266 A    7/1993
WO    WO 01/33921 A1 *    5/2001

* cited by examiner

*Primary Examiner*—Jurie Yun
(74) *Attorney, Agent, or Firm*—Sughrue Mion, PLLC

(57) ABSTRACT

A mammogram recording and read-out apparatus comprises a radiation image detector having a rectangular shape, a detector support section, and a breast support section. A support state of the detector support section is capable of being changed over between a first support state, in which the radiation image detector is supported in an orientation such that a short side of the radiation image detector stands facing the chest wall of an object, and a second support state, in which the radiation image detector is supported in an orientation such that a long side of the radiation image detector stands facing the chest wall of the object.

7 Claims, 7 Drawing Sheets

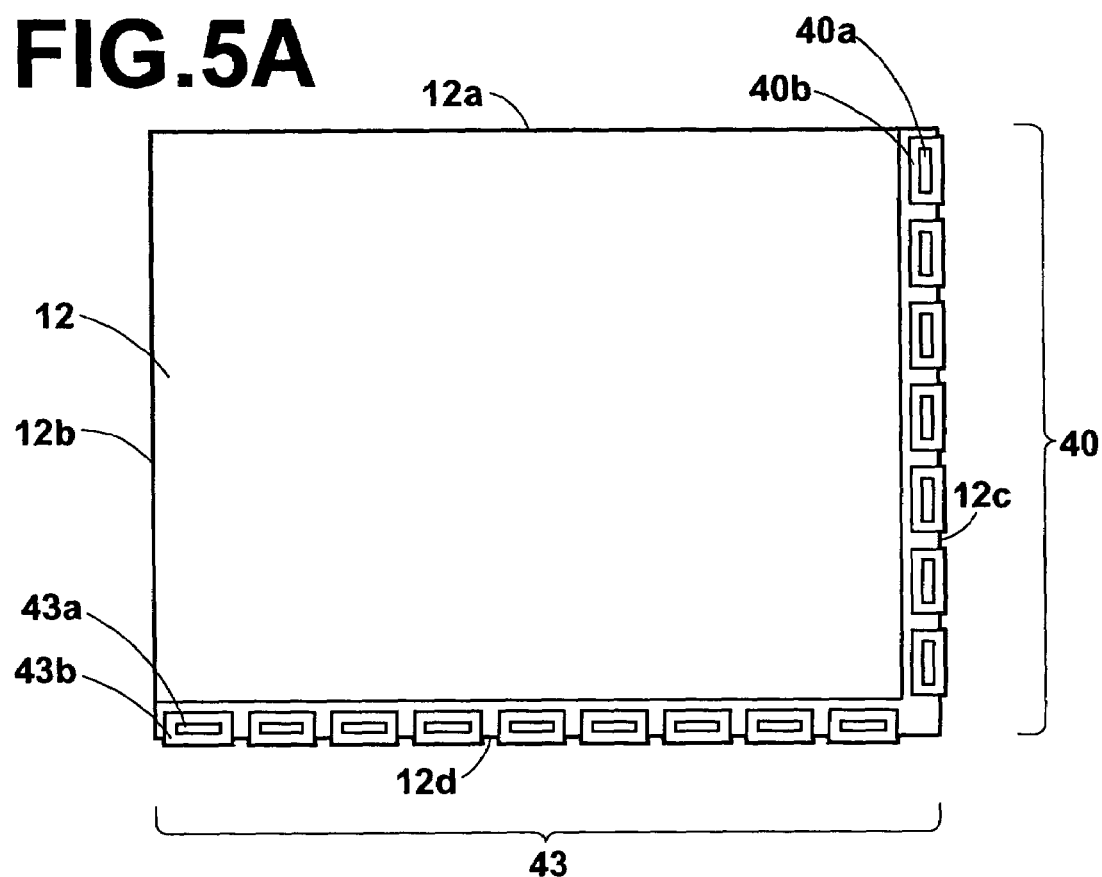
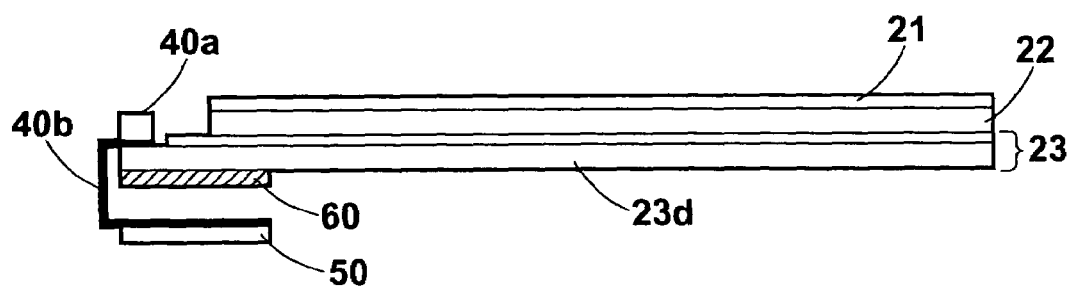

MAMMOGRAM RECORDING AND READ-OUT APPARATUS

BACKGROUND OF THE INVENTION

1. Field of the Invention

This invention relates to a mammogram recording and read-out apparatus comprising a radiation image detector, which is capable of recording a radiation image when it is exposed to radiation carrying image information. This invention particularly relates to a mammogram recording and read-out apparatus for use in operations for recording and reading out the radiation images of the breasts having different sizes.

2. Description of the Related Art

Various radiation image detectors for use in medical fields, and the like, have heretofore been proposed and used in practice. The radiation image detectors are capable of recording a radiation image of an object when being exposed to radiation carrying image information of the object and are capable of outputting an electric signal in accordance with the recorded radiation image.

Examples of the radiation image detectors include radiation image detectors utilizing semiconductor materials, which form electric charges when being exposed to the radiation. As the radiation image detectors utilizing the semiconductor materials, optical read-out types of radiation image detectors and TFT read-out types of radiation image detectors have heretofore been proposed.

As the optical read-out types of the radiation image detectors, there have been proposed the radiation image detectors comprising a first electrode layer, which has transmissivity to the radiation, a recording photo-conductor layer, which forms electric charges when it is exposed to the radiation having passed through the first electrode layer, a charge transporting layer, which acts as an insulator with respect to latent image charges and which acts as a conductor with respect to transported charges having a polarity opposite to the polarity of the latent image charges, a reading photo-conductor layer, which forms electric charges when it is exposed to reading light, and a second electrode layer constituted of a plurality of linear electrodes, which have transmissivity to the reading light and are arrayed in parallel. The first electrode layer, the recording photo-conductor layer, the charge transporting layer, the reading photo-conductor layer, and the second electrode layer are overlaid in this order.

As the TFT read-out types of the radiation image detectors, there have been proposed the radiation image detectors comprising an electrode layer, which has transmissivity to the radiation, a photo-conductor layer, which forms electric charges when it is exposed to the radiation having passed through the electrode layer, and an electric signal detecting layer, which is constituted of a plurality of detecting devices arrayed in a two-dimensional pattern. Each of the detecting devices is provided with a capacitor, which accumulates the electric charges having been formed in the photo-conductor layer, and a TFT switch for the reading of the electric charges from the capacitor. The electrode layer, the photo-conductor layer, and the electric signal detecting layer are overlaid in this order.

Also, various mammogram recording and read-out apparatuses for performing operations for recording and reading out X-ray images of the breasts have heretofore been proposed. (A mammogram recording and read-out apparatus is proposed in, for example, Japanese Unexamined Patent Publication No. 5(1993)-173266.) Further, mammogram recording and read-out apparatuses utilizing the radiation image detectors described above have been proposed.

In cases where the operations for recording and reading out the X-ray images of the breasts are performed by use of the mammogram recording and read-out apparatuses described above, since the sizes of the breasts vary for different persons to be examined, the problems described below occur. Specifically, for example, in cases where the size of the radiation image detector is smaller than the size of the breast, it is necessary for the image recording and read-out operations to be performed a plurality of times for different regions of the breast. In such cases, the dose delivered to the person to be examined is not capable of being kept small. Conversely, in cases where the size of the radiation image detector is larger than the size of the breast, for example, when the breast is sandwiched and compressed between a compression plate and the radiation image detector for the image recording and read-out operation, the problems occur in that, besides the breast, the abdomen is sandwiched between the compression plate and the radiation image detector, and the breast is not capable of being compressed sufficiently. Also, psychological burden given to the person to be examined is not capable of being kept light. Therefore, in the cases of the operations for recording and reading out the X-ray images of the breasts, it is necessary for the image recording and read-out operations to be performed by use of the radiation image detectors having the sizes in accordance with the sizes of the breasts.

However, the cost of the aforesaid radiation image detectors utilizing the semiconductor materials is high. Therefore, in cases where the radiation image detectors matched with the sizes of the breasts of the persons to be examined are prepared, the cost of the image recording and read-out apparatus is not capable of being kept low.

SUMMARY OF THE INVENTION

The primary object of the present invention is to provide a mammogram recording and read-out apparatus for performing operations for recording and reading out radiation images of the breasts having different sizes, wherein the operations for recording and reading out the radiation images are capable of being performed in a manner appropriate for the sizes of the breasts by used of a single same radiation image detector.

Another object of the present invention is to provide a mammogram recording and read-out apparatus for performing operations for recording and reading out radiation images of the breasts having different sizes, wherein the cost of the mammogram recording and read-out apparatus is capable of being kept low.

The present invention provides a mammogram recording and read-out apparatus, comprising:

i) a radiation image detector for operating such that:
   the radiation image detector forms electric charges when the radiation image detector is exposed to radiation carrying radiation image information of the breast of an object,
   the radiation image detector accumulates the thus formed electric charges and thereby records a radiation image of the breast of the object, and
   the radiation image detector outputs an electric signal in accordance with a quantity of the accumulated electric charges, ii) a detector support section for supporting the radiation image detector, and iii) a breast support section for supporting the breast of the object, the breast support section being located on the side of a surface of the radiation image detector, which surface is exposed to the radiation, wherein the radiation image detector has a rectangular shape, and a support state of the detector support section is capable of being changed over between a first support state, in which the radiation image detector is supported in an orientation such that a short side of the radiation image detector stands facing the chest wall of the object, and a second support state, in which the radiation image detector is supported in an orientation such that a long side of the radiation image detector stands facing the chest wall of the object.

The mammogram recording and read-out apparatus in accordance with the present invention may be modified such that the detector support section is provided with a rotating mechanism for rotating the radiation image detector in a plane of the radiation image detector and thereby changing over the support state of the detector support section between the first support state and the second support state.

Also, the mammogram recording and read-out apparatus in accordance with the present invention may be modified such that the radiation image detector is provided with a plurality of switches arrayed in a two-dimensional pattern, the electric signal being outputted from the radiation image detector through on-off operations of the switches, an actuating circuit for performing the on-off operations of the switches is located along only one side of the radiation image detector, which one side is other than the sides capable of being set to stand facing the chest wall of the object, and a detecting circuit for detecting the electric signal, which has been outputted from the radiation image detector, is located along only one side of the radiation image detector, which one side is other than the sides capable of being set to stand facing the chest wall of the object and is normal to the side provided with the actuating circuit.

Further, the mammogram recording and read-out apparatus in accordance with the present invention may be modified such that the mammogram recording and read-out apparatus further comprises a radiation blocking section for blocking impingement of the radiation upon a region of the radiation image detector, which region contains a short side of the radiation image detector opposite to the short side capable of being set to stand facing the chest wall of the object.

The breast support section may be a surface of a casing constituting the radiation image detector, which surface is located on the radiation irradiation side. Alternatively, the breast support section may be constituted as an independent section located on the radiation irradiation side of the radiation image detector. In cases where the breast support section is constituted as the independent section located on the radiation irradiation side of the radiation image detector, the breast support section may comprise, for example, a plate constituted of a member (such as a carbon plate or an acrylic resin plate), which has a sufficient transmissivity to the radiation and has a sufficient rigidity.

With the mammogram recording and read-out apparatus in accordance with the present invention, the radiation image detector has the rectangular shape. Also, the support state of the detector support section is capable of being changed over between the first support state, in which the radiation image detector is supported in the orientation such that the short side of the radiation image detector stands facing the chest wall of the object, and the second support state, in which the radiation image detector is supported in the orientation such that the long side of the radiation image detector stands facing the chest wall of the object. Therefore, in cases where the size of the breast is comparatively small, the radiation image detector may be set in the first support state. Also, in cases where the size of the breast is comparatively large, the radiation image detector may be set in the second support state. In this manner, the operations for recording and reading out the radiation image may be performed. In this manner, by use of only one radiation image detector, the operations for recording and reading out the radiation images of the breasts having different sizes are capable of being performed appropriately. Also, since it is sufficient for the only one radiation image detector to be used, the cost of the mammogram recording and read-out apparatus in accordance with the present invention is capable of being kept low.

The mammogram recording and read-out apparatus in accordance with the present invention may be modified such that the detector support section is provided with the rotating mechanism for rotating the radiation image detector in the plane of the radiation image detector and thereby changing over the support state of the detector support section between the first support state and the second support state. With the modification described above, the operation for changing over the support state of the detector support section between the first support state and the second support state is capable of being performed easily.

Also, the mammogram recording and read-out apparatus in accordance with the present invention may be modified such that the electric signal is outputted from the radiation image detector through the on-off operations of the plurality of the switches, which are arrayed in the two-dimensional pattern, the actuating circuit for performing the on-off operations of the switches is located along only one side of the radiation image detector, which one side is other than the sides capable of being set to stand facing the chest wall of the object, and the detecting circuit for detecting the electric signal, which has been outputted from the radiation image detector, is located along only one side of the radiation image detector, which one side is other than the sides capable of being set to stand facing the chest wall of the object and is normal to the side provided with the actuating circuit. With the modification described above, each of the sides of the radiation image detector, which sides are capable being set selectively so as to come into contact with the chest wall of the person to be examined, is free from the circuits. Therefore, the radiation image recording and read-out operations are capable of being performed with respect to the region of the breast, which region extends to the position markedly close to the chest wall of the person to be examined. Accordingly, the radiation image recording and read-out operations are capable of being performed appropriately such that a disease at a site in the vicinity of the chest wall of the person to be examined is capable of being detected.

Further, the mammogram recording and read-out apparatus in accordance with the present invention may be modified such that the mammogram recording and read-out apparatus further comprises the radiation blocking section for blocking the impingement of the radiation upon the region of the radiation image detector, which region contains the short side of the radiation image detector opposite to the short side capable of being set to stand facing the chest wall of the object. With the modification described above, the problems are capable of being prevented from occurring in that the radiation impinges upon the region of the radiation image detector other than the region, on which the breast lies. Therefore, the service life of the radiation image detector is capable of being kept long.

BRIEF DESCRIPTION OF THE DRAWINGS

FIG. 5A is a plan view showing an actuating circuit section and charge amplifiers of the radiation image detector of the mammogram recording and read-out apparatus of FIG. 1, FIG. 5B is a sectional view of FIG. 5A.

DESCRIPTION OF THE PREFERRED EMBODIMENTS

The present invention will hereinbelow be described in further detail with reference to the accompanying drawings.

Figure 1:
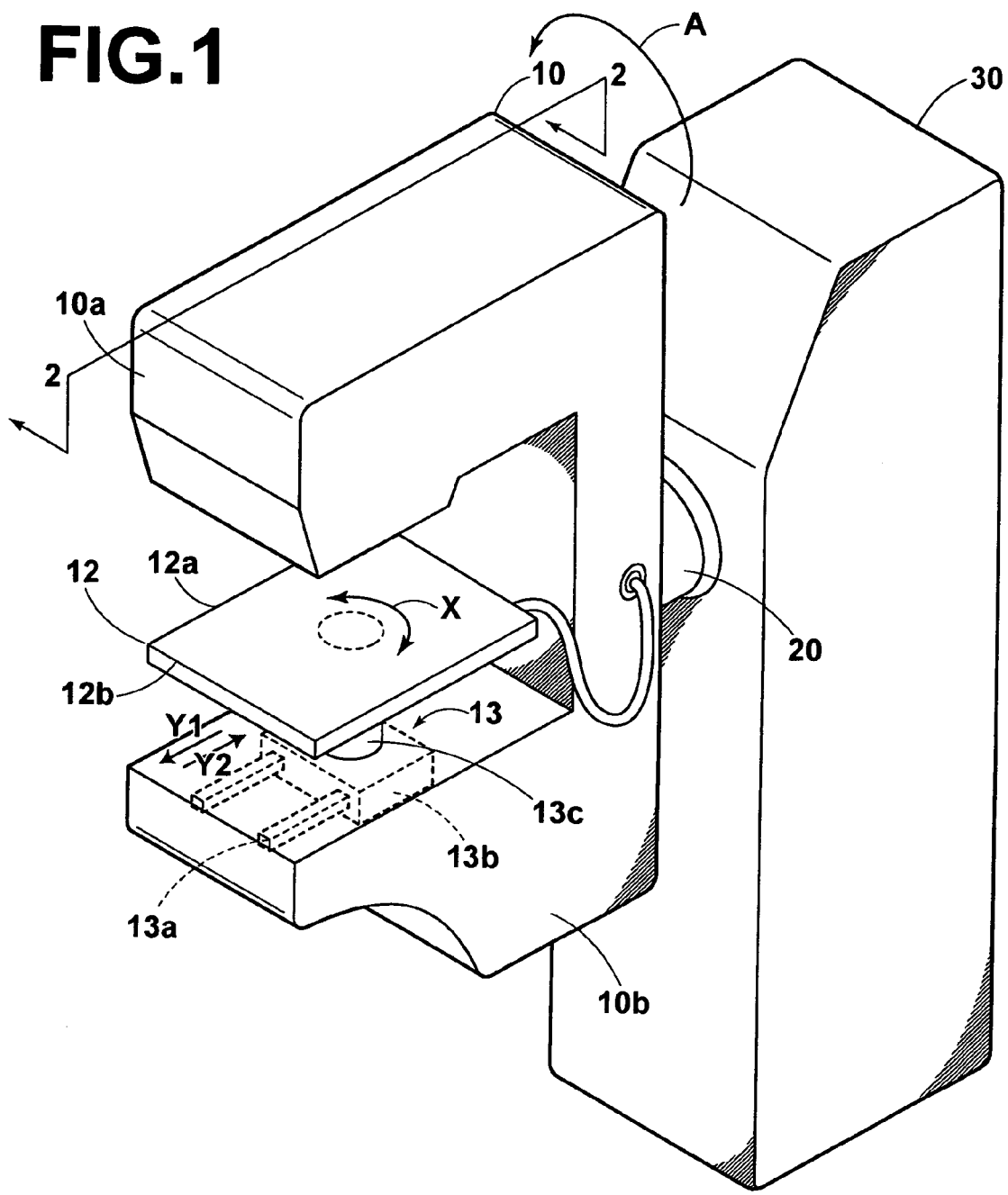
FIG. 1 is a schematic perspective view showing a mammogram recording and read-out apparatus, in which an embodiment of the mammogram recording and read-out apparatus in accordance with the present invention is employed.
Figure 2:
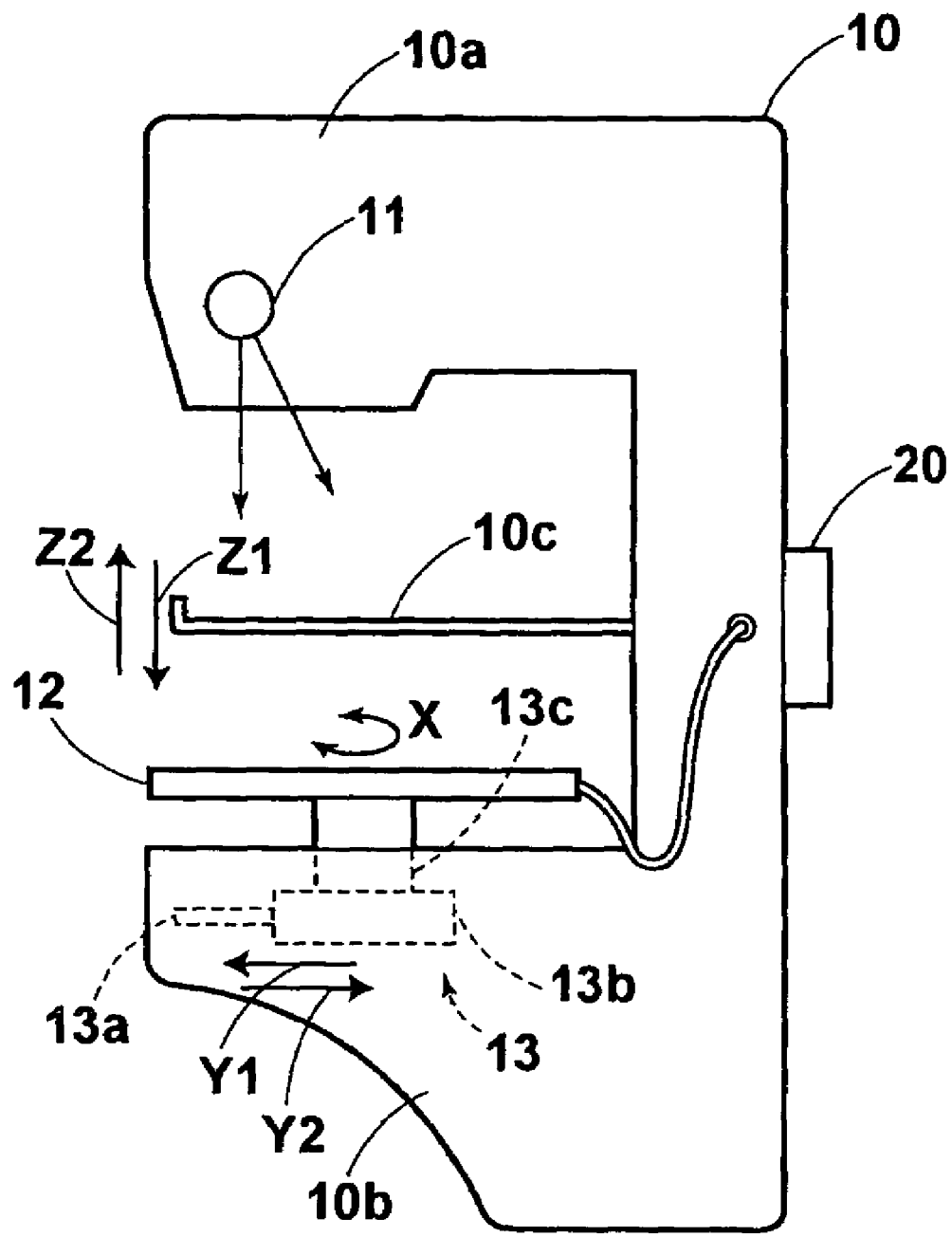
FIG. 2 is a sectional view taken on line 2—2 of FIG. 1.

FIG. 1 is a schematic perspective view showing a mammogram recording and read-out apparatus, in which an embodiment of the mammogram recording and read-out apparatus in accordance with the present invention is employed. FIG. 2 is a sectional view taken on line 2—2 of FIG. 1.

As illustrated in FIG. 1, the mammogram recording and read-out apparatus comprises a radiation image detector 12, which is capable of recording a radiation image of an object when it is exposed to radiation carrying image information of the object. The radiation image detector 12 has a rectangular shape. The mammogram recording and read-out apparatus also comprises an arm section 10 for supporting the radiation image detector 12. The arm section 10 is capable of being rotated in the direction indicated by the arrow A. The radiation image detector 12 further comprises a shaft section 20 for supporting the arm section 10 such that the arm section 10 is capable of being rotated. The radiation image detector 12 still further comprises a base 30, to which the shaft section 20 is secured.

As illustrated in FIG. 1 and FIG. 2, the arm section 10 is constituted in a U-shaped form. A radiation source 11 is located within a one end section 10a of the arm section 10. The radiation source 11 radiates out radiation toward the other end section 10b of the arm section 10. A detector support section 13 is located at the other end section 10b of the arm section 10. The detector support section 13 supports the radiation image detector 12, which is exposed to the radiation having been radiated out from the radiation source 11.

Also, as illustrated in FIG. 2, the arm section 10 comprises a compression plate 10c, which is located between the one end section 10a and the other end section 10b. The compression plate 10c is supported by the arm section 10 such that the compression plate 10c is capable of being moved in the direction indicated by the arrow Z1 and in the direction indicated by the arrow Z2. Radiation image recording and read-out operations are performed in the state, in which the breast of a person to be examined is sandwiched between the compression plate 10c and the radiation image detector 12 located at the detector support section 13 of the other end section 10b. The compression plate 10c is moved by a moving mechanism (not shown). In FIG. 1, the compression plate 10c is omitted for clearness. In the mammogram recording and read-out apparatus of FIG. 1, as described above, the surface of the radiation image detector 12, which surface is located on the radiation irradiation side, is constituted as the breast support section. Alternatively, a breast support section may be constituted as an independent section located on the radiation irradiation side of the radiation image detector 12. In cases where the breast support section is constituted as the independent section located on the radiation irradiation side of the radiation image detector 12, the breast support section may comprise, for example, a plate constituted of a member (such as a carbon plate or an acrylic resin plate), which has a sufficient transmissivity to the radiation and has a sufficient rigidity.

As illustrated in FIG. 1, the detector support section 13 is provided with rails 13a, 13a, which extend within the other end section 10b of the arm section 10. The detector support section 13 is also provided with a moving section 13b, which is capable of being moved along the rails 13a, 13a in the direction indicated by the arrow Y1 and in the direction indicated by the arrow Y2. The detector support section 13 is further provided with a rotating mechanism section 13c, which is secured to the moving section 13b. The rotating mechanism section 13c supports the radiation image detector 12, such that the radiation image detector 12 is capable of being rotated in the direction indicated by the arrow X.

The radiation image detector 12 is rotated by the rotating mechanism section 13c of the detector support section 13 and in the direction indicated by the arrow X. With the rotating mechanism section 13c, the support state of the detector support section 13 is capable of being changed over between a first support state, in which the radiation image detector 12 is supported in an orientation such that a short side 12b of the radiation image detector 12 comes into contact with the chest wall of the person to be examined, and a second support state, in which the radiation image detector 12 is supported in an orientation such that a long side 12a of the radiation image detector 12 comes into contact with the chest wall of the person to be examined.

Figure 3A:
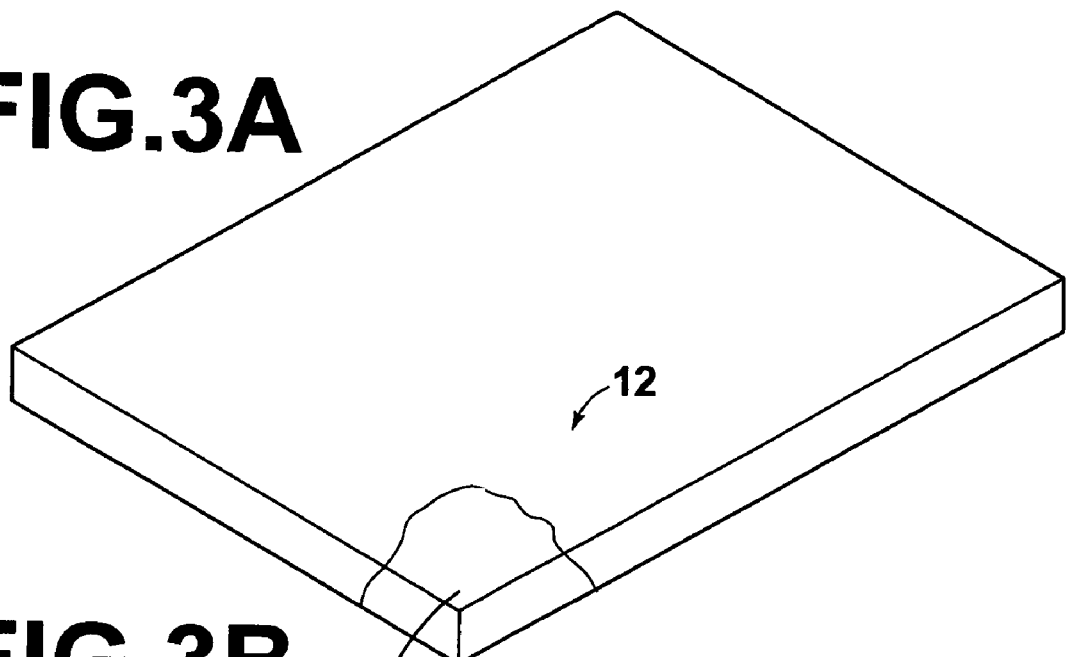
FIG. 3A is a perspective view showing a radiation image detector of the mammogram recording and read-out apparatus of FIG. 1.
Figure 3B:
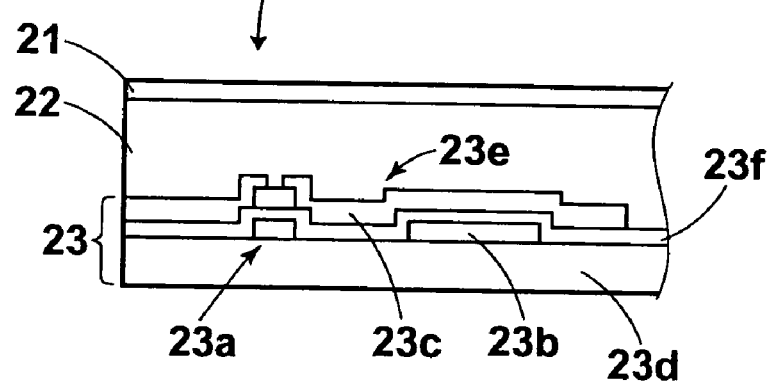
FIG. 3B is a sectional view showing part of the radiation image detector of FIG. 3A.

FIG. 3A is a perspective view showing the radiation image detector 12, which is supported by the detector support section 13. FIG. 3B is a sectional view showing part of the radiation image detector 12 of FIG. 3A.

As illustrated in FIG. 3A, the radiation image detector 12 has the rectangular shape. As illustrated in FIG. 3B, the radiation image detector 12 comprises an electrode layer 21, which has the transmissivity to the radiation. The radiation image detector 12 also comprises a photo-conductor layer 22, which forms electric charges when it is exposed to the radiation having passed through the electrode layer 21. The photo-conductor layer 22 is constituted of amorphous selenium and has a film thickness of 200 µm. The radiation image detector 12 further comprises an electric signal detecting layer 23 for detecting the electric charges, which have been formed in the photo-conductor layer 22, as an electric signal. The electrode layer 21, the photo-conductor layer 22, and the electric signal detecting layer 23 are overlaid in this order.

As illustrated in FIG. 3B, the electric signal detecting layer 23 is constituted of a plurality of detecting devices 23e, 23e, . . . , which are arrayed in a two-dimensional pattern on a surface of a glass plate 23d. Each of the detecting devices 23e, 23e, . . . comprises a thin film transistor (TFT) switch 23a, a pixel capacity element 23b, and a pixel electrode 23c.

Figure 4:
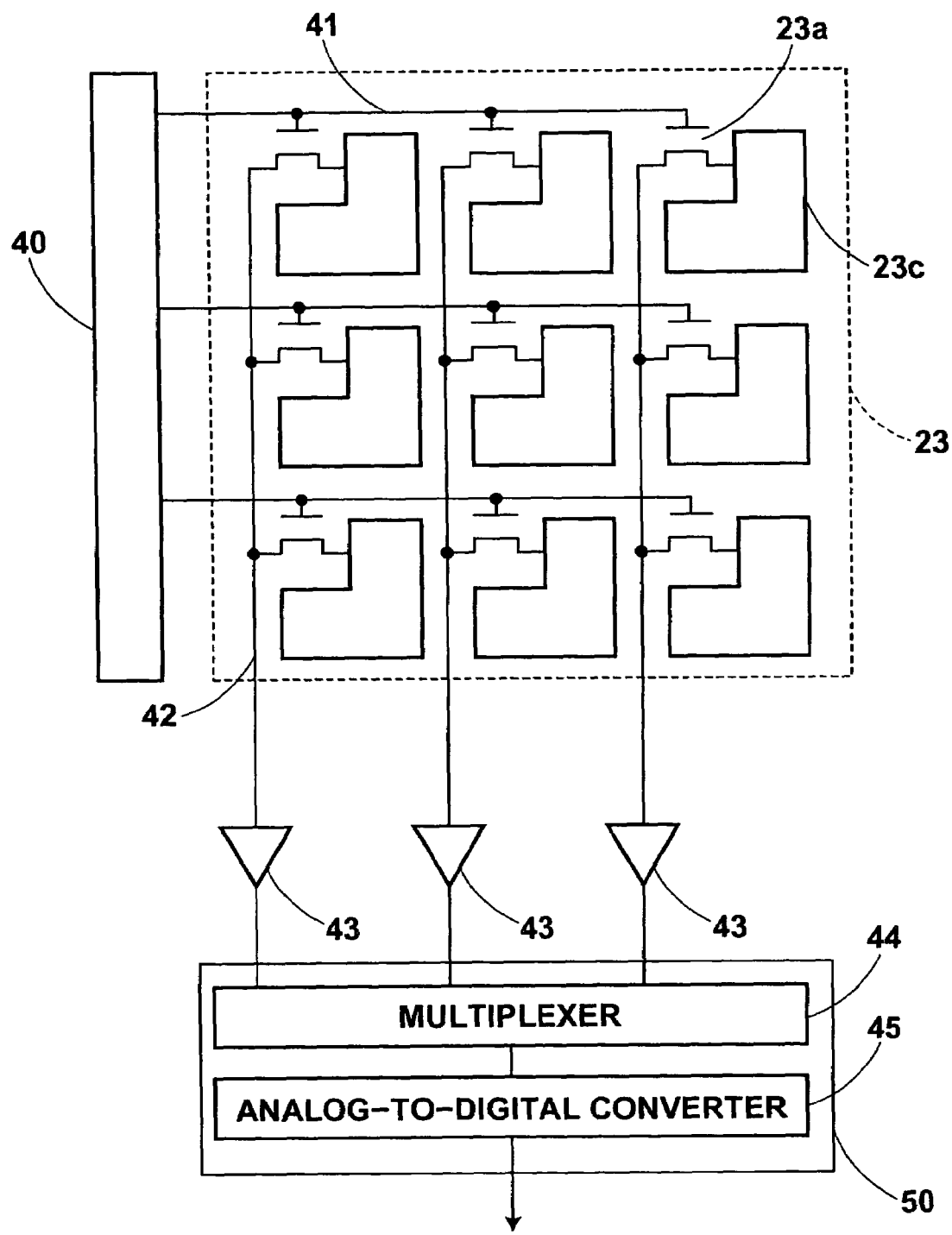
FIG. 4 is a detailed view showing part of the radiation image detector of FIG. 3A.

FIG. 4 is a plan view showing the electric signal detecting layer 23. The electric charges, which have been formed in the photo-conductor layer 22 when the photo-conductor layer 22 is exposed to the radiation, are accumulated in the capacitor, which is constituted of the pixel electrode 23c and the pixel capacity element 23b. The on-off operations of each of the TFT switches 23a, 23a, . . . are actuated by a control signal, which is given by an actuating circuit section 40 illustrated in FIG. 4, and through each of gate scanning lines 41, 41, . . . , which extend respectively along rows in the array of the TFT switches 23a, 23a, . . . Also, with the on-off operations of each of the TFT switches 23a, 23a, . . ., the electric charges having been accumulated in the capacitor connected to the TFT switch 23a are read out as the electric signal. The electric signal, which has been read out with the on-off operations of each of the TFT switches 23a, 23a, . . ., is outputted through the corresponding one of signal lines 42, 42, . . . The electric signal is then amplified by the corresponding one of charge amplifiers 43, 43, . . . The amplified electric signal passes through a multiplexer 44 and is then converted by an analog-to-digital converter 45 into a digital image signal. The array pitches of the detecting devices 23e, 23e, . . . of the radiation image detector 12, i.e. the pixel pitches, should preferably fall within the range of 50 µm to 100 µm.

As illustrated in FIG. 5A, the actuating circuit section 40 for performing the on-off operations of the TFT switches 23a, 23a, . . . of the radiation image detector 12 is secured as a group of IC chips 40a, 40a, . . . to the radiation image detector 12. Each of the IC chips 40a, 40a, . . . is mounted on a tape carrier package (TCP) 40b acting as a film base plate. The TCP 40b is bonded with a thermo-compression bonding technique to the corresponding gate scanning line 41 of the radiation image detector 12 via an anisotropic conductive film (ACF). Also, as illustrated in FIG. 5A, the plurality of the TCP's 40b, 40b, . . . , on which the IC chips 40a, 40a, . . . have respectively been mounted, are arrayed and located along only a short side 12c of the radiation image detector 12, which short side does not come into contact with the chest wall of the object.

Further, as illustrated in FIG. 5A, each of the charge amplifiers 43, 43, . . . for amplifying the electric signal having been outputted from the radiation image detector 12 is secured as IC chips 43a, 43a, . . . to the radiation image detector 12. Each of the IC chips 43a, 43a, . . . is mounted on a TCP 43b acting as a film base plate. The TCP 43b is bonded with a thermo-compression bonding technique to the corresponding signal line 42 of the radiation image detector 12 via an ACF. Also, as illustrated in FIG. 5A, the plurality of the TCP's 43b, 43b, . . . , on which the IC chips 43a, 43a, . . . have respectively been mounted, are arrayed and located along only a long side 12d of the radiation image detector 12, which long side does not come into contact with the chest wall of the object.

The IC chips 40a, 40a, . . . and the IC chips 43a, 43a, . . . are located in the manner described above. Therefore, in cases where the operations for recording and reading out the radiation image of the breast are performed, the radiation image recording and read-out operations are capable of being performed with respect to the region of the breast, which region extends to the position markedly close to the chest wall of the person to be examined. Accordingly, the radiation image recording and read-out operations are capable of being performed appropriately such that a disease at a site in the vicinity of the chest wall of the person to be examined is capable of being detected.

Furthermore, as illustrated in FIG. 5B, a printed circuit board 50, on which the multiplexer 44 and the analog-to-digital converter 45 have been mounted, is mounted on the TCP's 40b, 40b, . . . provided with the IC chips 40a, 40a, . . . Also, the TCP's 40b, 40b, . . . are bent such that the printed circuit board 50 may be located on the side of the radiation image detector 12 opposite to the side, to which the radiation is irradiated. Further, a radiation blocking plate 60 is located at the region of the glass plate 23d of the radiation image detector 12, which region stands facing the printed circuit board 50. The radiation blocking plate 60 blocks the impingement of the radiation, which has passed through the radiation image detector 12, upon the printed circuit board 50. The radiation blocking plate 60 may be made from, for example, lead.

How the mammogram recording and read-out apparatus described above operates will be described hereinbelow.

In cases where the radiation image recording and read-out operations are to be performed by use of the mammogram recording and read-out apparatus described above, firstly, the arm section 10 is rotated by an angle of 90 degrees in the direction indicated by the arrow A from the state illustrated in FIG. 1. Also, in accordance with the size of the breast, the operator selects whether the long side 12a or the short side 12b of the radiation image detector 12 is to be brought into contact with the chest wall of the person to be examined. For example, in cases where the short side 12b of the radiation image detector 12 is to be brought into contact with the chest wall of the person to be examined, the radiation image detector 12 is rotated by the rotating mechanism section 13c in the direction indicated by the arrow A and is set in the orientation such that the short side 12b of the radiation image detector 12 may be brought into contact with the chest wall of the person to be examined. (The state, in which the radiation image detector 12 is supported in the orientation such that the short side 12b of the radiation image detector 12 comes into contact with the chest wall of the person to be examined, is referred to as the first support state.) Also, for example, in cases where the long side 12a of the radiation image detector 12 is to be brought into contact with the chest wall of the person to be examined, the radiation image detector 12 is rotated by the rotating mechanism section 13c in the direction indicated by the arrow A and is set in the orientation such that the long side 12a of the radiation image detector 12 may be brought into contact with the chest wall of the person to be examined. (The state, in which the radiation image detector 12 is supported in the orientation such that the long side 12a of the radiation image detector 12 comes into contact with the chest wall of the person to be examined, is referred to as the second support state.)

In cases where the state, in which the radiation image detector 12 is supported, has been changed over from the first support state to the second support state, the moving section 13b is moved in the direction indicated by the arrow Y1 along the rails 13a, 13a, such that the long side 12a of the radiation image detector 12 is capable of coming into contact with the chest wall of the object, i.e. such that the long side 12a of the radiation image detector 12 is located at the position identical with the position, at which the short side 12b of the radiation image detector 12 was located in the first support state. Also, in cases where the state, in which the radiation image detector 12 is supported, has been changed over from the second support state to the first support state, the moving section 13b is moved in the direction indicated by the arrow Y2 along the rails 13a, 13a, such that the short side 12b of the radiation image detector 12 is capable of coming into contact with the chest wall of the object, i.e. such that the short side 12b of the radiation image detector 12 is located at the position identical with the position, at which the long side 12a of the radiation image detector 12 was located in the second support state.

Figure 6:
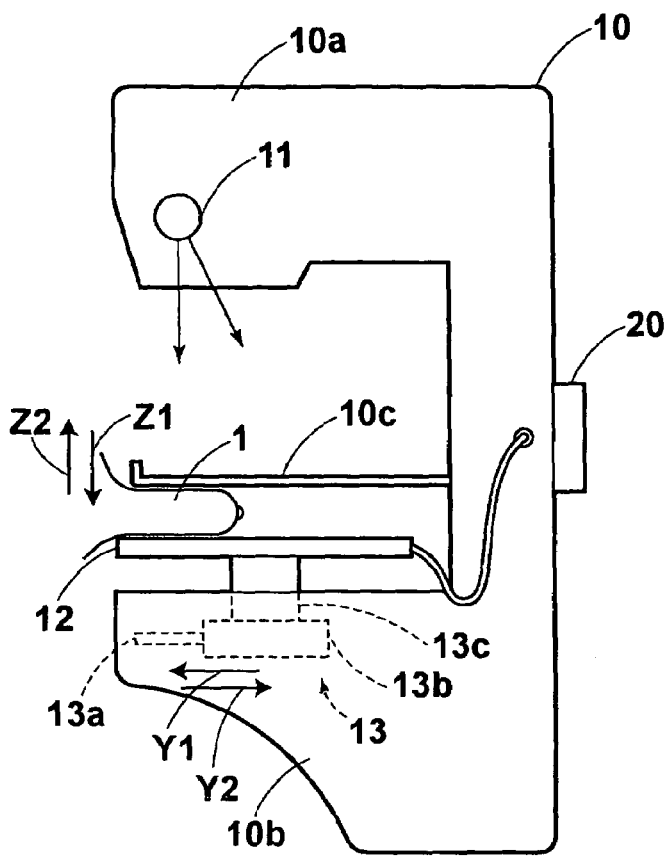
FIG. 6 is an explanatory view showing how the mammogram recording and read-out apparatus of FIG. 1 operates.

Also, as illustrated in FIG. 6, in the state in which the breast 1 lies between the radiation image detector 12 and the compression plate 10c, the compression plate 10c is moved in the direction indicated by the arrow Z1, and the breast 1 is sandwiched and supported between the radiation image detector 12 and the compression plate 10c. Thereafter, the radiation is radiated out from the radiation source 11. The radiation having been radiated out from the radiation source 11 passes through the compression plate 10c and the breast 1 and impinges upon the radiation image detector 12. The radiation, which has impinged upon the radiation image detector 12, passes through the electrode layer 21 and impinges upon the photo-conductor layer 22. As a result, in the photo-conductor layer 22, the electric charges are formed in accordance with the dose of the radiation. The thus formed electric charges are accumulated in the capacitors of the detecting devices 23e, 23e, . . . of the electric signal detecting layer 23. In this manner, the radiation image is recorded. Further, the on-off operations of the TFT switches 23a, 23a, . . . are performed in accordance with the control signal given by the actuating circuit section 40. With the on-off operations of the TFT switches 23a, 23a, . . . , the electric charges, which have been accumulated in the capacitors connected respectively to the TFT switches 23a, 23a, . . . , are read out a the electric signal. The thus read-out electric signal is outputted to the signal lines 42, 42, . . . and amplified by the charge amplifiers 43, 43, . . . The thus amplified electric signal is read out as the digital image signal via the multiplexer 44 and the analog-to-digital converter 45.

Figure 7A:
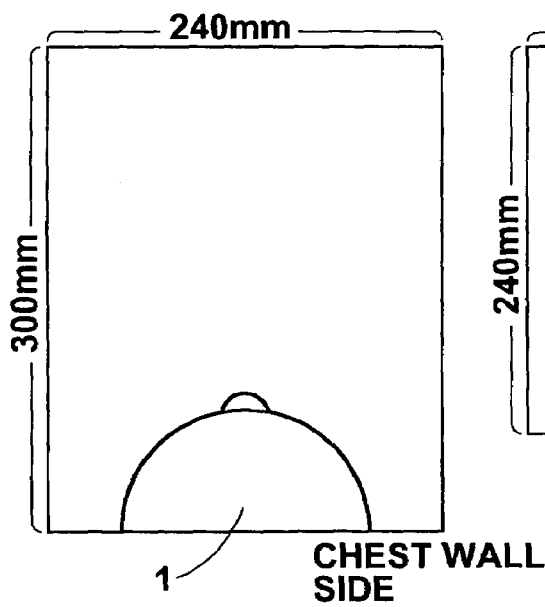
FIG. 7A is an explanatory view showing an example of a visible image obtained from the radiation image recording and read-out operations performed by the mammogram recording and read-out apparatus of FIG. 1.
Figure 7B:
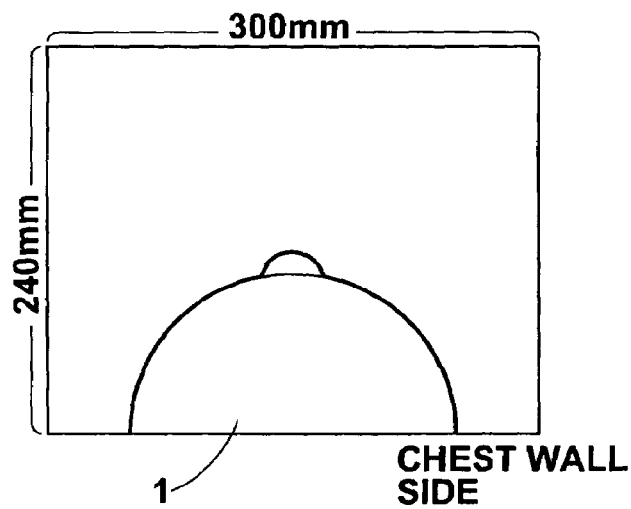
FIG. 7B is an explanatory view showing a different example of a visible image obtained from the radiation image recording and read-out operations performed by the mammogram recording and read-out apparatus of FIG. 1.

The digital image signal, which has been read out in the manner described above, is subjected to, for example, predetermined image processing, and is used for displaying a visible image on a monitor, or the like. In cases where the radiation image recording and read-out operations have been performed with the radiation image detector 12 being set in the first support state, and a visible image is reproduced and displayed on the monitor in accordance with the digital image signal having been read out from the radiation image detector 12, a visible image illustrated in FIG. 7A is obtained. Also, in cases where the radiation image recording and read-out operations have been performed with the radiation image detector 12 being set in the second support state, and a visible image is reproduced and displayed on the monitor in accordance with the digital image signal having been read out from the radiation image detector 12, a visible image illustrated in FIG. 7B is obtained. Each of the visible images illustrated in FIG. 7A and FIG. 7B is reproduced and displayed in accordance with the digital image signal, which represents the image having a size of 240 mm×300 mm. However, no limitation is imposed upon the size of the visible image.

With the mammogram recording and read-out apparatus described above, the radiation image detector 12 has the rectangular shape. Also, the support state of the detector support section 13 is capable of being changed over between the first support state and the second support state. Therefore, in cases where the size of the breast acting as the object is comparatively small, the radiation image detector 12 may be set in the first support state, such that the short side 12b of the radiation image detector 12 comes into contact with the chest wall of the person to be examined. Also, in cases where the size of the breast is comparatively large, the radiation image detector 12 may be set in the second support state, such that the long side 12a of the radiation image detector 12 comes into contact with the chest wall of the person to be examined. In this manner, the operations for recording and reading out the radiation image are capable of being performed. In this manner, by use of the only one radiation image detector 12, the operations for recording and reading out the radiation images of the breasts having different sizes are capable of being performed appropriately.

Figure 8:
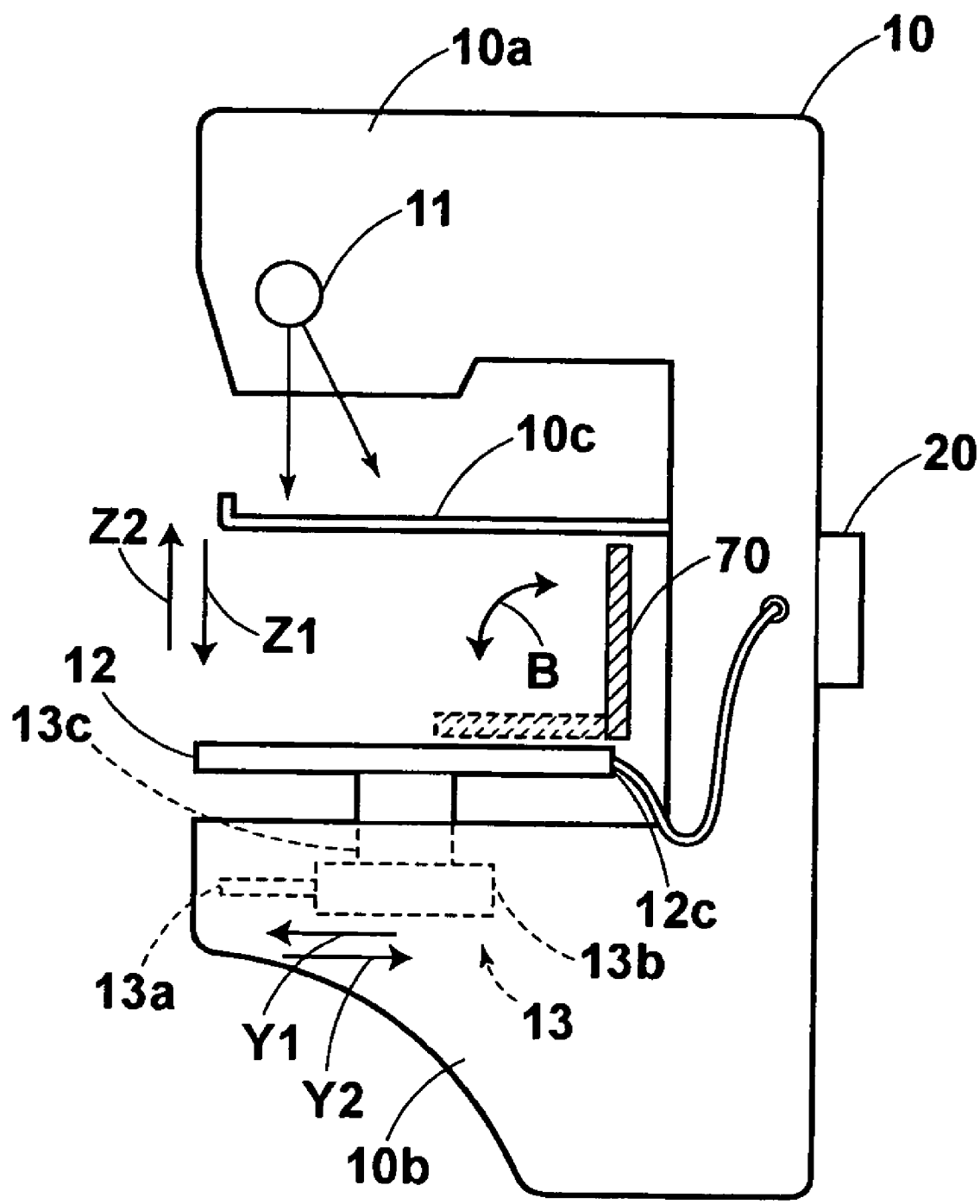
FIG. 8 is a schematic view showing a mammogram recording and read-out apparatus, in which a different embodiment of the mammogram recording and read-out apparatus in accordance with the present invention is employed.

FIG. 8 is a schematic view showing a mammogram recording and read-out apparatus, in which a different embodiment of the mammogram recording and read-out apparatus in accordance with the present invention is employed. The mammogram recording and read-out apparatus of FIG. 8 is provided with a radiation blocking section 70. In cases where the radiation image recording and read-out operations are performed with the radiation image detector 12 being set in the first support state, such that the radiation may not impinge upon the region of the radiation image detector 12, which region contains the short side 12c that does not come into contact with the chest wall of the person to be examined, the radiation blocking section 70 is located so as to block the impingement of the radiation upon the aforesaid region of the radiation image detector 12. The radiation blocking section 70 may be constituted of a plate made from lead, or the like. The radiation blocking section 70 is capable of being rotated in the direction indicated by the arrow B. Only in cases where the radiation image recording and read-out operations are performed with the radiation image detector 12 being set in the first support state, the radiation blocking section 70 is rotated to the position which stands facing the radiation image detector 12.

With the mammogram recording and read-out apparatus provided with the radiation blocking section 70, the problems are capable of being prevented from occurring in that the radiation impinges upon the region of the radiation image detector 12 other than the region, on which the breast lies. Therefore, the service life of the radiation image detector 12 is capable of being kept long.

With the mammogram recording and read-out apparatus described above, the radiation image recording and read-out operations may be performed in a state, in which grid for absorbing scattered radiation occurring at the object is located at the radiation image detector 12. In such cases, it is necessary that the grid is not rotated when the support state of the radiation image detector 12 is changed over. For such purposes, the operator may remove the grid from the radiation image detector 12 and may then again locate the grid at the radiation image detector 12 after the support state of the radiation image detector 12 has been changed over. Alternatively, the mammogram recording and read-out apparatus may be provided with a mechanism for automatically retracting the grid from the radiation image detector 12 and for again automatically locating the grid at the radiation image detector 12 after the support state of the radiation image detector 12 has been changed over. The grid is provided with radiation absorbing regions, which are made from a material, such as lead, and radiation transmitting regions, which do not absorb the radiation and transmit the radiation and is made from an intermediate material, such as wood, paper, or aluminum. The radiation absorbing regions and the radiation transmitting regions of the grid are located alternately. With the grid, the scattered radiation is absorbed and removed by the radiation absorbing regions.

In the embodiments described above, the TFT read-out type of the radiation image detector is employed. Alternatively, the optical read-out type of the radiation image detector may be employed. As the light source for the optical read-out type of the radiation image detector, an electroluminescent (EL) light source having a planar shape may be utilized.

What is claimed is:

1. A mammogram recording and read-out apparatus, comprising:
   i) a radiation image detector for operating such that:
      the radiation image detector forms electric charges when the radiation image detector is exposed to radiation carrying radiation image information of the breast of an object,
      the radiation image detector accumulates the thus formed electric charges and thereby records a radiation image of the breast of the object, and
      the radiation image detector outputs an electric signal in accordance with a quantity of the accumulated electric charges,
   ii) a detector support section for supporting the radiation image detector, and
   iii) a breast support section for supporting the breast of the object, the breast support section being located on the side of a surface of the radiation image detector, which surface is exposed to the radiation,
   wherein the radiation image detector has a rectangular shape, and
   a support state of the detector support section is capable of being changed over between a first support state, in which the radiation image detector is supported in an orientation such that a short side of the radiation image detector stands facing the chest wall of the object, and a second support state, in which the radiation image detector is supported in an orientation such that a long side of the radiation image detector stands facing the chest wall of the object.

2. An apparatus as defined in claim 1 wherein the detector support section is provided with a rotating mechanism for rotating the radiation image detector in a plane of the radiation image detector and thereby changing over the support state of the detector support section between the first support state and the second support state.

3. An apparatus as defined in claim 1 wherein the radiation image detector is provided with a plurality of switches arrayed in a two-dimensional pattern, the electric signal being outputted from the radiation image detector through on-off operations of the switches,
   an actuating circuit for performing the on-off operations of the switches is located along only one side of the radiation image detector, which one side is other than the sides capable of being set to stand facing the chest wall of the object, and
   a detecting circuit for detecting the electric signal, which has been outputted from the radiation image detector, is located along only one side of the radiation image detector, which one side is other than the sides capable of being set to stand facing the chest wall of the object and is normal to the side provided with the actuating circuit.

4. An apparatus as defined in claim 2 wherein the radiation image detector is provided with a plurality of switches arrayed in a two-dimensional pattern, the electric signal being outputted from the radiation image detector through on-off operations of the switches,
   an actuating circuit for performing the on-off operations of the switches is located along only one side of the radiation image detector, which one side is other than the sides capable of being set to stand facing the chest wall of the object, and
   a detecting circuit for detecting the electric signal, which has been outputted from the radiation image detector, is located along only one side of the radiation image detector, which one side is other than the sides capable of being set to stand facing the chest wall of the object and is normal to the side provided with the actuating circuit.

5. An apparatus as defined in claim 1 wherein the apparatus further comprises a radiation blocking section for blocking impingement of the radiation upon a region of the radiation image detector, which region contains a short side of the radiation image detector opposite to the short side capable of being set to stand facing the chest wall of the object.

6. An apparatus as defined in claim 2 wherein the apparatus further comprises a radiation blocking section for blocking impingement of the radiation upon a region of the radiation image detector, which region contains a short side of the radiation image detector opposite to the short side capable of being set to stand facing the chest wall of the object.

7. An apparatus as defined in claim 3 wherein the apparatus further comprises a radiation blocking section for blocking impingement of the radiation upon a region of the radiation image detector, which region contains a short side of the radiation image detector opposite to the short side capable of being set to stand facing the chest wall of the object.

* * * * *